United States Patent [19]

Haskell

[11] Patent Number: 5,524,473

[45] Date of Patent: Jun. 11, 1996

[54] GAS CHROMATOGRAPH FLOW CALIBRATOR

[76] Inventor: Weston W. Haskell, Box 553, Fulshear, Tex. 77441-0553

[21] Appl. No.: 368,491

[22] Filed: Jan. 1, 1995

[51] Int. Cl.[6] .................................................. G01N 31/00
[52] U.S. Cl. .......................................................... 73/1 G
[58] Field of Search .................... 73/1 G, 23.41; 137/606, 896

[56] References Cited

U.S. PATENT DOCUMENTS

| | | | |
|---|---|---|---|
| 3,665,748 | 5/1972 | Mator | 73/1 G |
| 3,693,403 | 9/1972 | Paul | 73/30 |
| 3,894,419 | 7/1975 | Mator et al. | 73/1 G |
| 4,003,240 | 1/1977 | Durbin | 73/1 G |
| 4,096,746 | 6/1978 | Wilson et al. | 73/205 R |
| 4,224,279 | 9/1980 | Tsang et al. | 422/78 |
| 4,905,497 | 3/1990 | Shindo et al. | 73/1 G |
| 5,092,217 | 3/1992 | Achter et al. | 86/1.1 |
| 5,175,431 | 12/1992 | Eisele et al. | 250/288 |
| 5,191,786 | 3/1993 | Baughman et al. | 73/64.45 |
| 5,214,952 | 6/1993 | Leggett et al. | 73/1 G |
| 5,239,856 | 8/1993 | Mettes et al. | 73/1 G |
| 5,261,452 | 11/1993 | McAndrew et al. | 137/606 |

Primary Examiner—Robert Raevis

[57] ABSTRACT

An apparatus for calibrating a gas chromatograph. Calibration accuracy to the limits of the detection accuracy of a gas chromatograph is achieved by a flow calibration apparatus that incorporates two particle filters and two fluid column bubblers.

4 Claims, 4 Drawing Sheets

GAS CHROMATOGRAPH FLOW CALIBRATOR

SUMMARY OF THE INVENTION a. Field of Invention

Gas chromatographs are well known, well understood, well developed instruments and are virtually the only instrument capable of analyzing complex gas mixtures. Gas chromatograph results are expressed as peak areas for the component of interest. The peak area is linearly proportional to concentration of the component of interest. However, to deduce concentrations from the peak area requires that, at least one time someone has run a calibration gas mixture into the same gas chromatograph. The results of a gas chromatograph analysis can be expressed as follows:

$$Px=(Ax/Ac)*Pc$$

Where Px is the percent volume of x in-the sample mixture; Pc is the percent volume of x in the calibration mixture; Ax is the area of x recorded by the gas chromatograph; and Ac is the area of x recorded by the gas chromatograph during calibration.

Now it can be appreciated that the gas chromatograph derived concentrations, Px are subject to the errors involved in making the "calibration" gas mixture containing the component, x. Let Tx be the unknown true concentration of x in the calibration mixture. If the label on the calibration tank lists Pc as 1.02 x Tc then all the gas chromatograph results for component x will be too high by that same factor of 1.02. The purpose of the present approach is to calibrate a gas chromatograph with sufficient accuracy to define the relationship between Pc and Tc. Prior to the present calibration method the relationship between Pc and Tc could not be defined.

The calibration method taught here starts with a pure component x and dilutes this component with, for instance, nitrogen to a known volumetric ratio and defines the uncertainty limits on the volumetric ratio in the normal course of carrying out this calibration.

Accordingly, the present invention relates to the field of apparatus for and methods of calibrating gas chromatographs.

More particularly, the present invention relates to apparatus for and methods of calibrating gas chromatographs which utilize flow dilution of a known hydrocarbon gas stream into an inert carrier gas stream to obtain a calibration sample quantity of the known hydrocarbon gas.

Yet more particularly, the present invention relates to apparatus for and methods of calibrating gas chromatographs which utilize flow dilution of a known hydrocarbon gas stream into an inert carrier gas stream to obtain a calibration sample quantity of the known hydrocarbon gas and which utilize pressure regulation of a gas stream into a known flow restriction to calibrate the flow rate of both the inert carrier gas stream and the known hydrocarbon gas stream.

b. Background of the Invention

Prior art in the field of apparatus for and methods of calibrating gas chromatographs includes the utilization of pressure regulators and flow restrictors on both the known hydrocarbon gas stream and the inert carrier gas stream. However, difficulties have arisen in maintaining repeatability of pressure regulation and flow rates over time. Primarily the limitations on the accuracy of gas chromatographs are the limitations on knowing the flow rates of the known hydrocarbon gas stream and of the inert carrier gas stream. Limitations on knowing the flow rates of the known hydrocarbon gas stream and of the inert carrier gas stream are caused by limitations on the pressure regulation of the gas streams.

A substantial need exists for apparatus and methods of calibrating gas chromatographs which include the utilization of pressure regulators and flow restrictors on both the known hydrocarbon gas stream and the inert carrier gas stream.

An additional need exists for such above-described apparatus and methods of calibrating gas chromatographs which include the utilization of pressure regulators and flow restrictors on both the known hydrocarbon gas stream and the inert carrier gas stream and which maintain repeatability of pressure regulation and flow rates over time.

A further need exists for such above-described apparatus and methods of calibrating gas chromatographs which include the utilization of pressure regulators and flow restrictors on both the known hydrocarbon gas stream and the inert carrier gas stream and which maintain repeatability of pressure regulation and flow rates over time by improving pressure regulation of the gas streams.

Accordingly, it is a primary object of this invention to provide apparatus and methods of calibrating gas chromatographs which include the utilization of pressure regulators and flow restrictors on both the known hydrocarbon gas stream and the inert carrier gas stream.

It is another object of this invention to provide apparatus and methods of calibrating gas chromatographs which include the utilization of pressure regulators and flow restrictors on both the known hydrocarbon gas stream and the inert carrier gas stream and which maintain repeatability of pressure regulation and flow rates over time.

It is a further and final object of this invention to provide apparatus and methods of calibrating gas chromatographs which include the utilization of pressure regulators and flow restrictors on both the known hydrocarbon gas stream and the inert carrier gas stream and which maintain repeatability of pressure regulation and flow rates over time by improving pressure regulation of the gas streams.

DESCRIPTION OF THE PREFERRED EMBODIMENT

Figure 1:
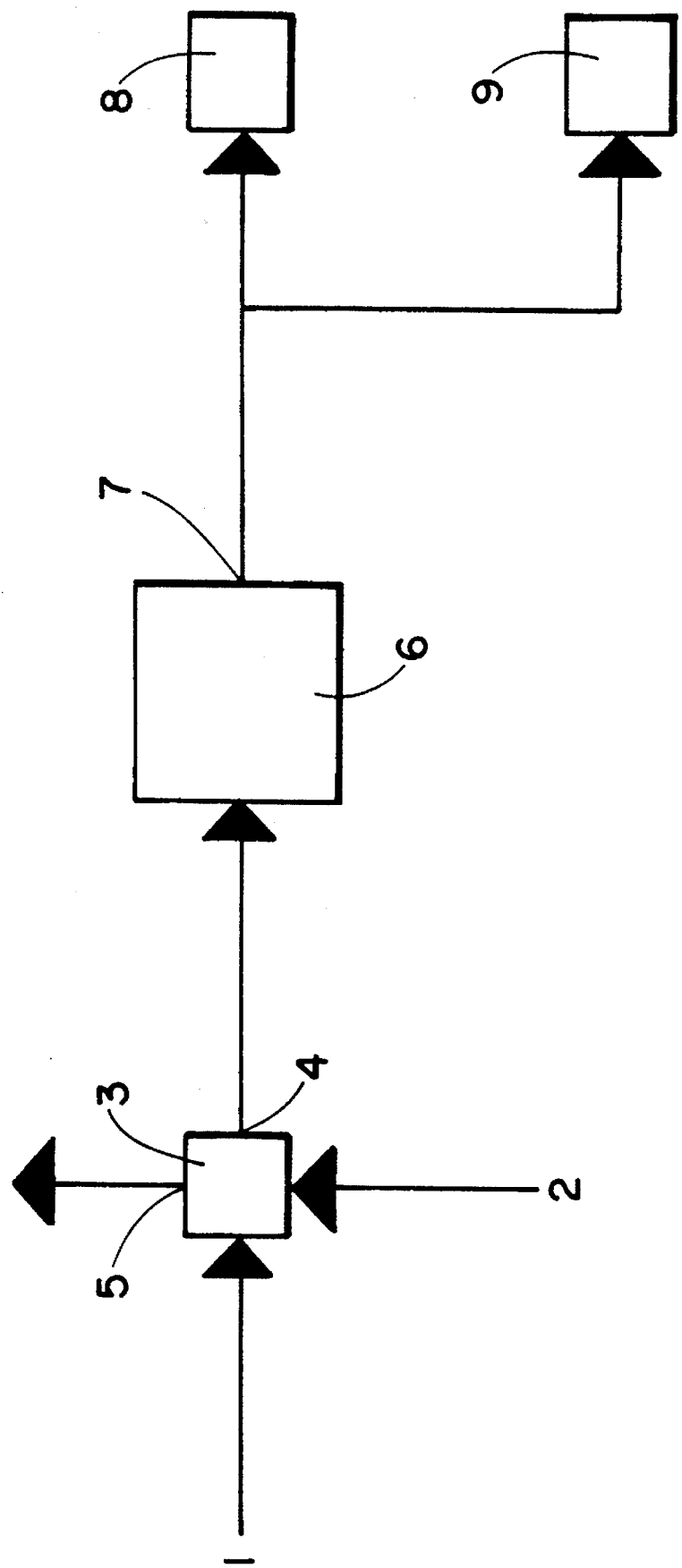
FIG. 1 is a block diagram of the calibration set-up of a gas chromatograph.

The standard calibration set-up for a gas chromatograph (6) is seen in FIG. 1. Such set-up begins with a source of a known hydrocarbon gas (1) having a known concentration and a source of an inert carrier gas (2). A sample quantity of the known hydrocarbon gas is inserted into the flow of the inert carrier gas by means of a sample valve (3). The output of the sample valve (3) is either vented away from the gas chromatograph (6) through sample valve vent (5) or input to the gas chromatograph (6) through sample valve output (4), depending on the rotational position of the sample valve (3). The gas chromatograph output (7) is to a hydrogen flame ionization detector (8) and/or to a thermal conductivity detector (9).

A thermal conductivity detector (9) is usually a simple tube with a central hot wire. A thermal conductivity detector (9) responds to any gas having a different conductivity than the carrier gas, Response is measured with a thermocouple or thermistor to measure the change (signal may increase or decrease) in temperature. Thermal conductivity detectors (9) respond best, and very close to linearly, versus the volume fraction of the sample gas in a carrier, for example Argon gas or Helium gas, gas stream.

A hydrogen flame ionization detector (8) is a device which utilizes a hydrogen-air flame which generates a very low background level of ionization. When organic substances are present in the hydrogen-air gas stream then ionization increases in exact proportion to the concentration of organic vapor present. The ion concentration is sensed in a hydrogen flame ionization detector (8) by imposing a potential, say 300 volt, across the flame. Hydrogen flame ionization detectors (8) respond linearly to weight fraction of organic vapor present in the flame.

Figure 2:
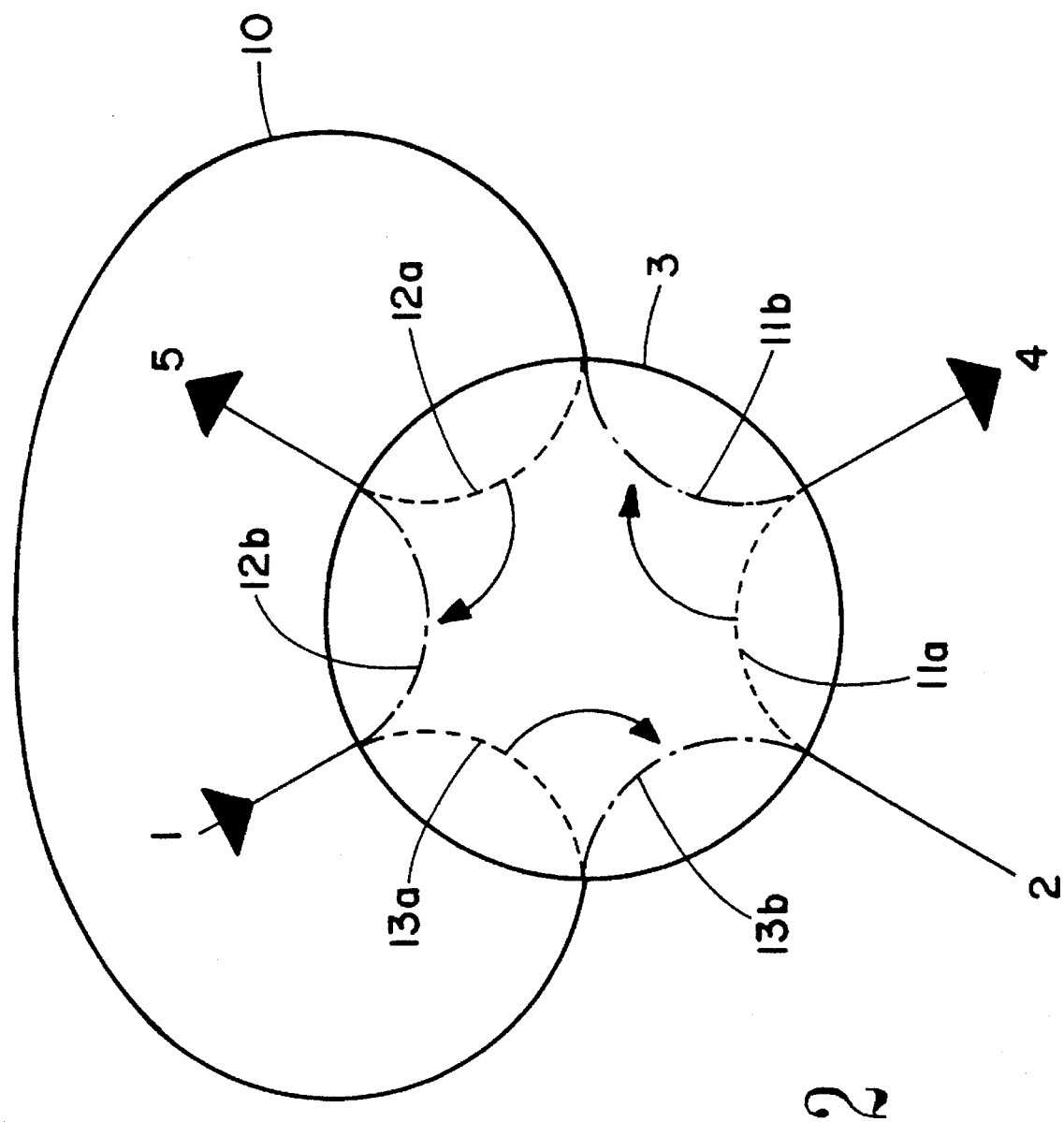
FIG. 2 is a schematic diagram of a gas sample valve.

As seen in both FIG. 1 and FIG. 2, the sample valve (3) is a two position gas flow valve. The two positions of the sample valve (3) in FIG. 2 are shown by designating the flow paths (11, 12, and 13) as an "a" position path or a "b" position path. When the sample valve (3) is in position "a" the gas flow paths (11a, 12a, and 13a) are in use. When the sample valve (3) is in position "b" the gas flow paths (11b, 12b, and 13b) are in use. The sample valve (3) additionally provides a sample gas loop (10) through which the known hydrocarbon gas flows from line 1 via gas flow paths (13a) and (13b) to the sample valve vent (5) when the sample valve (3) is in the "a" position. When the sample valve (3) is placed in the "b" position, the quantity of known hydrocarbon gas which is instantaneously within the sample gas loop (10) is pushed by carrier gas from line 2, through the gas flow path (13b), sample gas loop (10) and (11b) of the sample valve (3), to sample valve output (4) and thence to the gas chromatograph (6).

Referring back to FIG. 1, a gas chromatograph (6) is typically capable of detecting gaseous input components, both hydrocarbon and inert, to a precision of 0.05% in the current state of the art. However, current calibration techniques in use for the gas chromatograph (6) introduce unknown errors in the composition reports.

The limited accuracy of gas chromatograph (6) composition reports under the current state of the art occurs as a result of the way that calibration of the gas chromatograph (6) is done. Typically, in the current state of the art, calibration of the gas chromatograph (6) is accomplished by using a gas calibration cylinder as the source of the known hydrocarbon gas (1). In some cases, the known hydrocarbon gas and the known inert gas are combined into a single gas calibration cylinder. Some manufacturers of gas calibration cylinders weight into the cylinder each gaseous component.

Consider a gas calibration cylinder weighting 20 kilograms. On a balance scale capable of accuracy to one part in 100,000, the uncertainty and possible error is 0.20 gram in mg. If one mole of methane 24 liter is added to a 20 mg. gas calibration cylinder at standard conditions, the added methane will have a mass of 16 gram. At the very best the weight of methane loaded into the cylinder will be known to 16 plus or minus 2*0.2 gram or 0.4 gram or about 2% accuracy. Of course, the mass of all the other components will be subject to the same uncertainty but other hydrocarbon components are heavier and so will be known relatively more accurately.

Therefore, the best gas chromatograph calibration gas cylinders, under the current state of the art, will be loaded with methane to 2% accuracy, assuming the heavier components do not significantly absorb on the cylinder walls. The assumption of no significant absorption is not valid when a hydrocarbon as heavy as butane is present.

Figure 3:
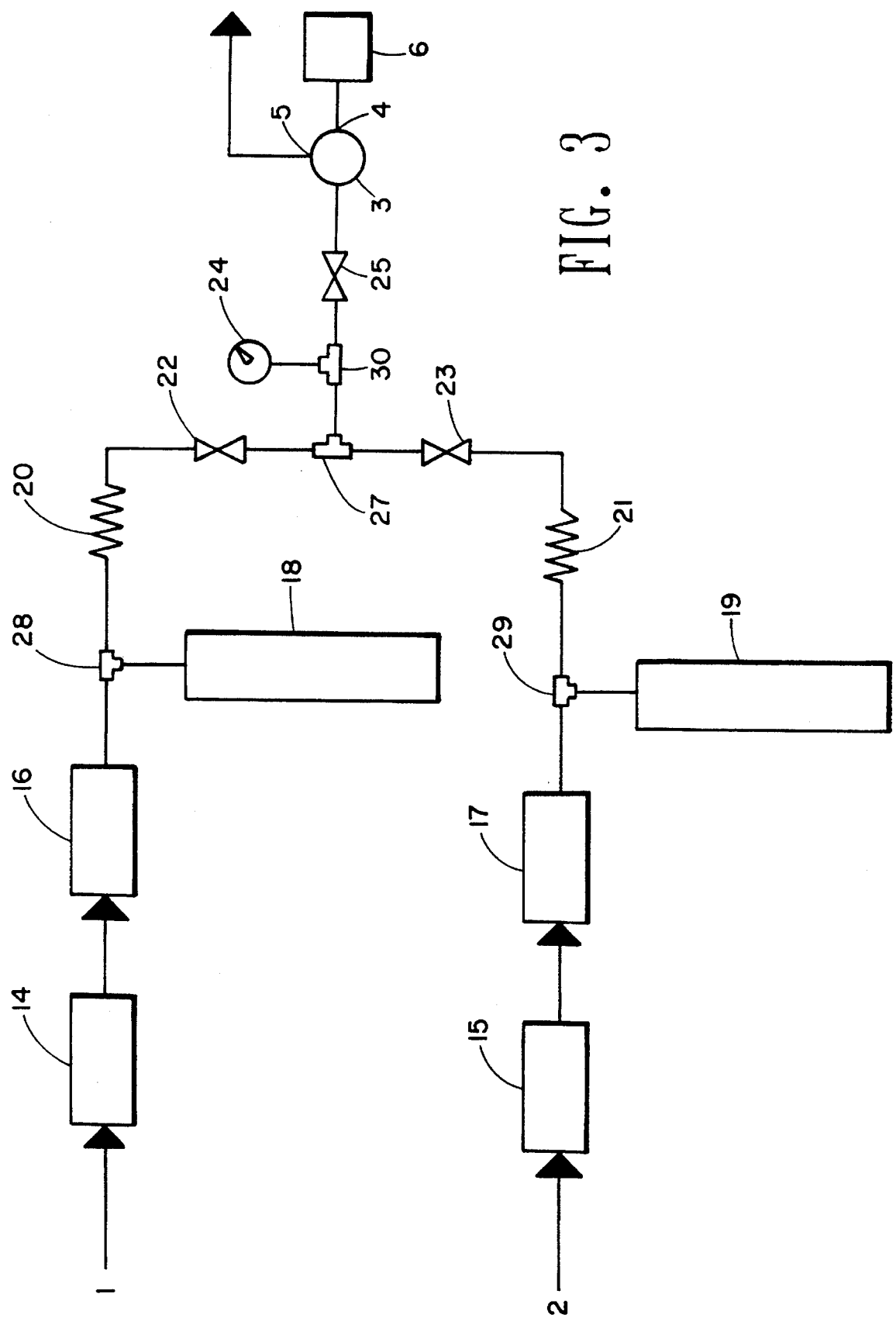
FIG. 3 is a schematic diagram of the apparatus of the instant invention, set-up to calibrate a gas chromatograph.

A more accurate calibration method is to flow dilute a known hydrocarbon gas with an inert or non-organic gas, such as nitrogen. The flow dilution system of gas chromatograph (6) calibration, which is utilized in the instant invention, see FIG. 3, consists of sources of two gases, a known source of hydrocarbon gas (1) and a known source of inert carrier gas (2). The known source of hydrocarbon gas (1) is connected through a fine particle filter (14) to a gas pressure regulator (16), which in turn has its output connected to a T connector (28) which splits the gas flow between the input of a length of, for example, 0.003 inch diameter capillary tubing (20) and the input of a fluid column gas bubbler (18). The capillary tubing (20) is cut to length to attain the desired gas flow with 10 psig on the output of the gas pressure regulator (16). The output of the capillary tubing (20) is input to an on/off gas shut off valve (22).

The known source of inert carrier gas (2) is connected through a fine particle filter (15) to a gas pressure regulator (17), which has its output connected to a T connector (29) which splits the gas flow between the input of a length of 0.003 inch diameter capillary tubing (21) and the input of a fluid column gas bubbler (19). The capillary tubing (21) is cut to length to attain the desired gas flow with 10 psig on the output of the gas pressure regulator (17). The output of the capillary tubing (21) is input to an on/off gas shut off valve (23).

The outputs of the flow restrictors (20 and 21) are input to the T connector (27) where mixing of the gases occurs. The gas pressure regulators (16 and 17) must be set to the same pressure to avoid one of the two gases from backing up into the flow line for the other gas through the T connector (27). Although backup of one gas into the flow line for the other gas can be minimized by using a sensitive check valve at either end of on/off gas shut off valves (22) and (23), it is better to minimize the driving force of back dilution of either gas.

The output of the T connector (27) is to the input of another T connector (30). The outputs of the T connector (30) are to a pressure gauge (24) and to an adjustable valve flow restrictor (25). The adjustable valve flow restrictor (25) must be adjusted to achieve the desired pressure on the pressure gauge (24). The output of the adjustable valve flow restrictor (25) is connected via sample valve output (4) to the input of the gas chromatograph (6).

If the gas chromatograph (6) of the instant invention has both a hydrogen flame ionization detector (8) and a thermal conductivity detector (9), as shown in FIG. 1, or only a thermal conductivity detector (9), connected to its output, then both components of the gaseous mixture can be detected. The performance of the flow dilution system of the instant invention was assessed by repeated runs on the gas chromatograph (6).

Utilizing a standard, not of the instant invention, calibration method for a gas chromatograph (6), the typical pattern encountered is that one component area, as measured on the gas chromatograph (6), will decrease with time while the other component area increases with time. This means that the flow of one component is increasing or that the flow of the other component is decreasing. Experience has shown that flows that are small enough to be measured by a soap film meter will change with time even with the best pressure regulators (16 and 17). After working with a standard calibration method for the gas chromatograph (6) for a period of time, it was discovered that the pressure regulators (16 and 17) must be protected from dust particles by use of 0.2 micron pore, or smaller, size filters (14 and 15). Smaller pore sizes are available for the filters (14 and 15), but smaller pore sizes create a higher pressure drop at a given flow and are sensitive to plugging by captured particles.

Figure 4:
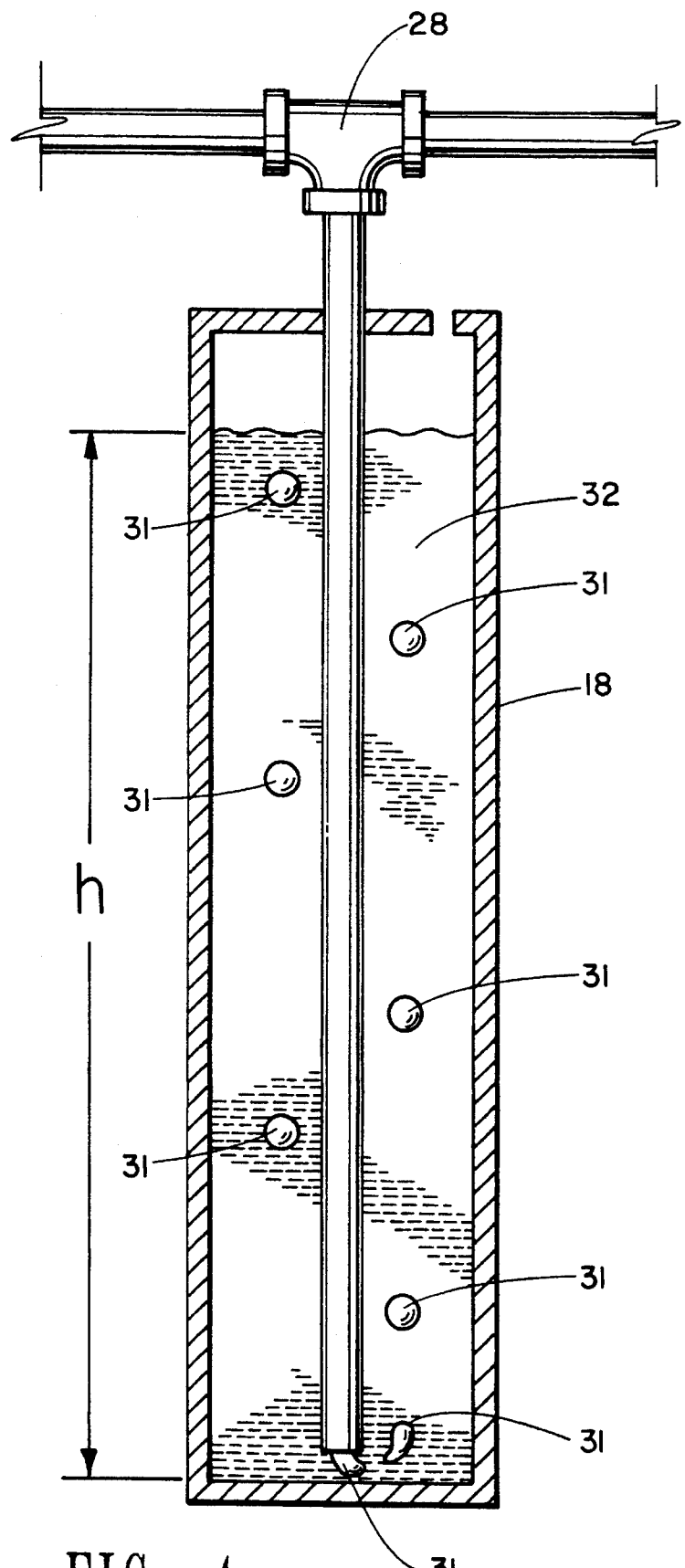
FIG. 4 is a lateral view of the fluid column bubbler of the instant invention, together with its input connections.

Even after taking all possible precautions to remove particulate matter from each of the gas streams, gas pressure regulators (16 and 17) still exhibited long term trends in the gas flow from the associated capillary tubing flow restrictors (20 and 21). To attain a steady pressure in each of the gas streams, the output of each of the gas pressure regulators (16 and 17) were input to fluid column bubblers (18 and 19) having a 12 foot head of water (32), ie. about 10 psig pressure. See FIG. 4. The gas flow bypassed into the fluid column bubbler (18 and 19) was adjusted by the setting of the pressure regulator (16 and 17). The pressure regulators (16 and 17) were adjusted to give a few bubbles (31) per minute in the fluid column bubblers (18 and 19) at the time that the sample gas was being bypassed to the gas chromatograph from the known hydrocarbon gas and the known inert (nitrogen) gas streams. That is, at a time that the sample valve (3) was in position to pass a sample quantity of mixed, diluted sample gas to the sample gas loop (10), see FIG. 2, and from the sample gas loop (10) to the input of the gas chromatograph (6) when the sample valve (3), see FIGS. 1 and 2, is switched to position "b" as described above.

Utilization of the fluid column bubblers (18 and 19), of the instant invention, in conjunction with the particle filters (14 and 15), of the instant invention, in a standard flow dilution calibration of gas chromatograph (6), resulted in a gas flow composition that did not change with time over a continuous sampling period of three days. Thus, the technique produced a known and documented dilution of the input gases.

The technique of the instant invention improves on the long term constancy of a pressure regulator (16 or 17) by using super clean pressure regulator preceded by a 0.2 micron filter to prevent transport of dust by the inlet gas stream. The presence of dust in the pressure regulator (16 and 17) acts to make the pressure at the output of the pressure regulator (16 and 17) erratic or worse, exhibit a long term trend.

Even with the addition of the dust filters (14 and 15) to the standard flow dilution gas chromatograph (6) flow dilution method of calibration, as above-described, the pressure of the gas stream input to the gas chromatograph (6), as measured at the pressure guage (24), exhibits long term trends. To avoid these trends the pressure regulator (16 and 17) outlets were input into 12 foot high columns of water (32) in fluid column bubblers (18 and 19). The pressure regulator (16 and 17) output pressure was then adjusted to produce about two bubbles per minute. Use of the fluid column bubblers (18 and 19) will deliver constant pressure at the inputs to the T connector (27) as long as the pressure regulators (16 and 17) output pressure stays just above the 12 foot fluid column pressure of the fluid column bubblers (18 and 19).

It must be realized that the fluid column pressure limits will operate only in combination with a certain range of pressure regulation. Obviously, if the pressure falls below the column pressure then there is no longer any benefit of the fluid column. Conversely, if the pressure rises too much above the column regulator start to bypass gas then the bypass flow rate will increase to a point where the viscous pressure drop along the pipe will be come large enough to raise the pressure above the column bubble point pressure. That is why this apparatus works only in combination with using high quality dust free pressure regulators and feeding the gas to same with a large area filter with a pore size of less than 0.2 micron.

The instant invention, with dust filters (14 and 15) and fluid column bubblers (18 and 19) maintains constant pressure at the input to the capillary tube gas flow restrictors (20 and 21).

The flow dilution achieved by the method of the instant invention, as tested by the gas chromatograph (6) output readings, was constant over a period of three days. The flow of methane, as a known hydrocarbon gas, and nitrogen, as a known inert (non-reactive, non-hydrocarbon) gas, was restarted five minutes before beginning sampling over the three day (72 hour) period and produced a constant area for the methane peak. Approximately 300 gas chromatograph runs were made over the three day test period. The methane calibration was determined within an error of 0.2% volume.

The 0.2% volume error in setup and method of the instant invention was caused by the uncertainty in gas flow readings in the commercial soap film flow meter which was utilized to measure gas flow rates. The commercial soap film flow meter utilized was clearly designed to be produced at minimum cost. The digital readout displays of the commercial soap film flow meter utilized were only of three digits. Repeated readings on the commercial soap film flow meter utilized lead to exactly the same three digits as the pressure reading for the gas flow. This repetition of the output reading means that whatever variations in gas flow rate existed were not observed with this design soap film meter. Three digit precision was sufficient for practical uses for which this commercial soap film meter was made. With the setup and method of the instant invention, it would be worthwhile to design a soap film flow meter capable of significantly greater accuracy since the apparatus of the instant invention can generate two separate gas flows that are repeatable to better than three significant figures.

Soap film flow meters consist of a glass tube of known volume between two etched lines (fiducial marks). The volume between the two etched lines can be determined by the distance between the lines and the inside diameter of the tube. Alternatively, the glass tube can be filled with water from a calibrated burette, which in turn can be checked by weighing the water delivered or if that is not sufficiently accurate by filling with mercury and weighing the delivered mercury. Thus, the volume between the fiducial marks can be determined to the desired accuracy, but if the same soap film meter is employed to measure the flows of the two gases, then any uncertainty involving the volume between the fiducial marks will cancel. However, time measurement must be made to the desired accuracy. Currently, time is routinely measured to one part in $10^{14}$!. Thus, any practical timing accuracy can be achieved.

It is inherent in the design of the instant invention that the absolute accuracy of the flow rate measurement be determined in the course of setting up the flows of each gas. Therefore, practically, ten repeat measurements of the flow rates of each gas are made. From these measurements of the gas flow rates any desired parameter can be deduced in which to express the precision of the measurement of each gas flow rate. Because of volume of the gas tube of the soap film flow meter cancels out between the ratio of the two gas flows, the accuracy of the flow dilution is known to the precision of the ratio of the gas flows, e.g.

Let F1 be the flow of gas "1"
Let F2 be the flow of gas "2"
Let the observed time for the bubble to traverse the two fiducial marks on the glass tube of the soap film flow meter be T1 for gas "1" at the given condition.
Then $$F1=V/T1$$

For the gas "2" we have a similar measurement yielding T2 for the time of traverse. Thus, $$F2=V/T2$$

The dilution of gas "1" in the mixture of "1" and "2" is then given by:

$$VF(1)=F1/(F1+F2)=V/T1/(V/T1+V/T2) \qquad 1)$$

The top and bottom of the right side of equation 1 can be divided by V, giving $$VF(1)=(1/T1)/(1/T1+1/T2) \qquad 2)$$

Thus, the dilution is known to an accuracy and precision determined by the precision of the time interval measurement. Electronic techniques permit time intervals to be determined to far more accuracy than the repeatability of the system will allow.

The method and apparatus of the instant invention have been shown to be curative of the problem resultant from and inherent in all other known methods of calibrating a gas chromatograph. That problem cured is that the composition of the hydrocarbon sample gas can now be known to an accuracy with defined error limits.

This invention and its operation have been described in terms of a single preferred embodiment; however, numerous embodiments are possible without departing from the essential characteristics thereof. Accordingly, the description has been illustrative and not restrictive as the scope of the invention is defined by the appended claims, not by the description preceding them, and all changes and modifications that fall within the stated claims or form their functional equivalents are intended to be embraced by the claims.

I claim:

1. Apparatus useful for the calibration of a gas chromatograph utilizing the flow dilution method of calibration comprising:

a source of a known hydrocarbon gas of known dilution;
a first 0.2 micron, or smaller, pore size dust filter;
a first pressure regulator;
a first T connector;
a first fluid column bubbler;
a first capillary tube flow restrictor;
a first flow restrictor valve;
and further comprising:
a source of a known inert gas;
a second 0.2, or smaller, micro pore dust filter;
a second pressure regulator;
a second T connector;
a second fluid column bubbler;
a second capillary tube flow restrictor;
a second flow restrictor valve;
and further comprising:
a third T connector;
and further comprising:
a fourth T connector;
a pressure gauge;
a sample valve; and
a gas chromatograph;
wherein
said source of a known hydrocarbon gas of known dilution is connected to the input of said first 0.2, or smaller, micro pore dust filter;
the output of said first 0.2, or smaller, micro pore dust filter is connected to the input of said first pressure regulator;
the output of said first pressure regulator is connected to the input of said first T connector;
one output of said first T connector is connected to the input of said first fluid column bubbler;
the second output of said first T connector is connected to the input of said first capillary tube flow restrictor;
the output of said first capillary tube flow restrictor is connected to one input of said third T connector; and, further,
said source of a known inert gas is connected to the input of said second 0.2, or smaller, micro pore dust filter;
the output of said second 0.2, or smaller, micro pore dust filter is connected to the input of said second pressure regulator;
the output of said second pressure regulator is connected to the input of said second T connector;
one output of said second T connector is connected to the input of said second fluid column bubbler;
the second output of said second T connector is connected to the input of said second capillary tube flow restrictor;
the output of said second capillary tube flow restrictor is connected to the second input of said third T connector; and, further,
the output of said third T connector is connected to the input of said fourth T connector;
one output of said fourth T connector is connected to the input of said on/off valve;
the second output of said fourth T connector is connected to the input of said pressure gauge;
the output of said on/off valve is connected to the input of said sample valve; and
the output of said sample valve is connected to the input of said gas chromatograph.

2. The apparatus of claim 1 wherein the output of said gas chromatograph is connected to the input of a thermal conductivity detector.

3. The apparatus of claim 1 wherein the output of said gas chromatograph is connected to the input of a hydrogen flame ionization detector.

4. The apparatus of claim 1 wherein the output of said gas chromatograph is connected to the input of a thermal conductivity detector and to the input of a hydrogen flame ionization detector.

* * * * *